United States Patent [19]

Brown et al.

[11] Patent Number: 4,547,903
[45] Date of Patent: Oct. 22, 1985

[54] SWEAT BAND APPARATUS

[76] Inventors: Larry L. Brown, 807 W. Minnesota, Lantana, Fla. 32460; Jerry H. Lisle, 109 18th St., Belleair Beach, Fla. 22535

[21] Appl. No.: 908,573

[22] Filed: May 22, 1978

Related U.S. Application Data

[63] Continuation-in-part of Ser. No. 672,779, Apr. 1, 1976, abandoned.

[51] Int. Cl.⁴ .............................................. A61F 9/04
[52] U.S. Cl. ............................................. 2/12; 2/199; 2/DIG. 6
[58] Field of Search ............... 2/183, 197, 181, 181.4, 2/181.2, 182.2, 195, 175, 12, DIG. 6, 199, 171.3

[56] References Cited

U.S. PATENT DOCUMENTS

| | | | |
|---|---|---|---|
| 1,156,487 | 10/1915 | Kunstadter | 2/197 UX |
| 1,258,617 | 3/1918 | Fritsch | 2/12 |
| 1,977,983 | 10/1934 | Carter | 2/181 |
| 2,019,028 | 10/1935 | Sternberg | 2/12 |
| 2,446,053 | 7/1948 | Matarazzo | 2/197 |
| 2,447,850 | 8/1948 | Feldman | 2/197 |
| 2,994,090 | 8/1961 | Ostwald | 2/183 X |
| 3,487,472 | 1/1970 | Lewtan | 2/183 |
| 3,837,005 | 9/1974 | Persson | 2/199 X |
| 4,023,212 | 5/1977 | Huffman | 2/197 |
| 4,131,953 | 1/1979 | Kimotsuki | 2/171.3 X |

FOREIGN PATENT DOCUMENTS

| | | | |
|---|---|---|---|
| 1259571 | 3/1961 | France | 2/197 |
| 0021870 | of 1905 | United Kingdom | 2/197 |

OTHER PUBLICATIONS

Gershman, "Self-Adhering Nylon Tapes", 10-18-58, J.A.M.A., vol. 168, No. 7, p. 930.
Sporting Goods Business, "Sweat Bands for Head and Wrist", 5/8/72.

Primary Examiner—Peter Nerbun

[57] ABSTRACT

A sweat band made of a moisture absorbing material is shaped to fit around the head of a person and has strips of hook and loop material attached thereto for attaching a sun visor or cap. The sun visor has a concave curved portion shaped to fit the forehead of the user and a strip of hook and loop material attached to the visor curved portion so that a molded plastic visor can be attached and detached as needed by the user. The cap has a portion removed from the rear crown and sweat band and a moisture absorbing sweat band is removably attached to the cap's sweat band with hook and loop material. The moisture absorbing sweat band is elasticized and can expand in the removed portion of the crown and cap sweat band.

11 Claims, 7 Drawing Figures

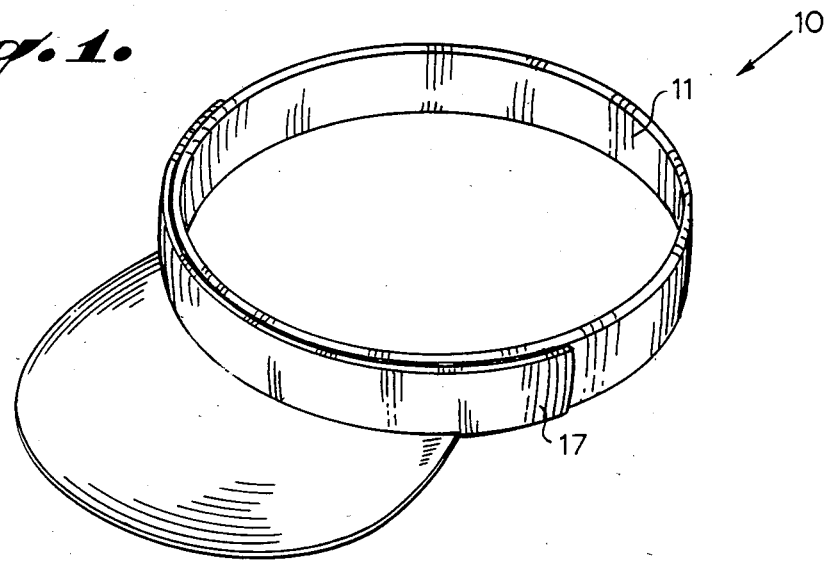
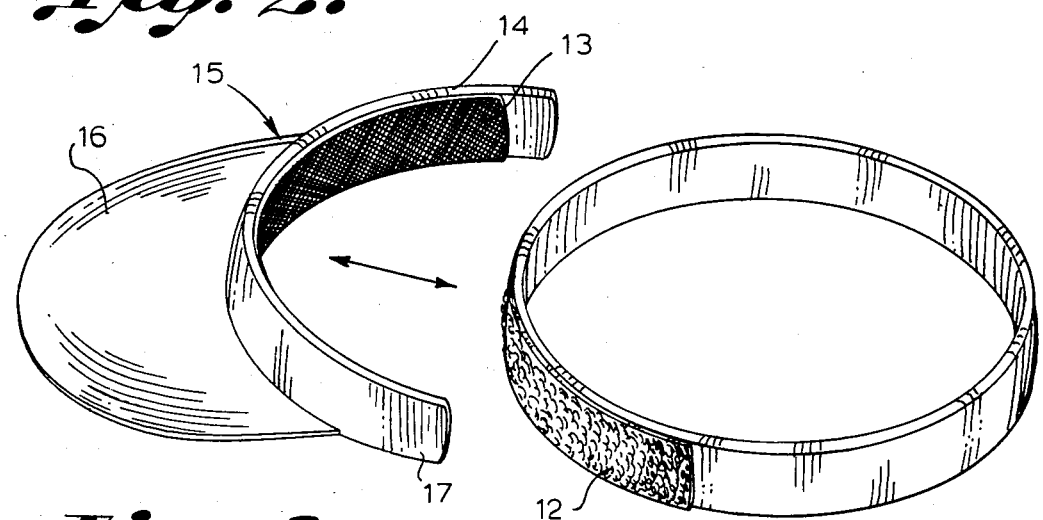
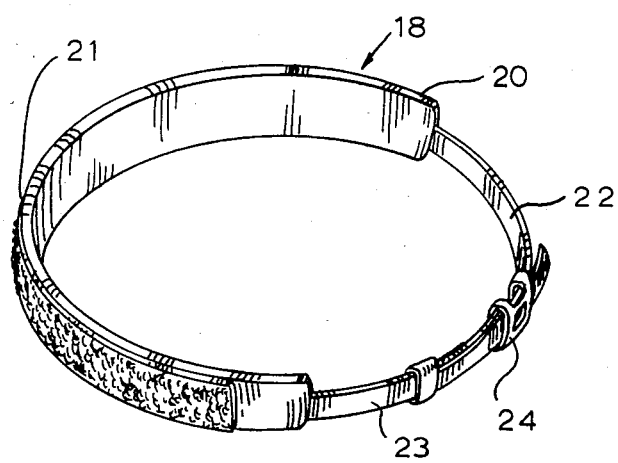

SWEAT BAND APPARATUS

This application is a continuation-in-part of application Ser. No. 672,779, filed 04/01/76, now abandoned.

BACKGROUND OF THE INVENTION

The present invention relates to a sweat band removably attached to a molded plastic visor or to a cap.

In the past, it has been common to have a great variety of sweat bands for absorbing the sweat on the forehead of an individual during sporting activities such as playing tennis or a great variety of other sports. Typically, such sweat bands are made of a moisture absorbing material to absorb the sweat on the forehead to prevent it from rolling down the face into the eyes and to help keep the individual cool. It has also been common in the past to provide various types of caps having visor fronts and visors for shading the sun from the eyes of the user during sporting activities such as playing golf, tennis, or the like. It has also been known to combine these functions and to add sweat bands to caps for use in sporting events.

A number of prior U.S. Patents have dealt with sweat bands and visors, and these include U.S. Pat. No. 1,809,956, which teaches an eye shield which has a visor and a head encircling bandeau which functions as a perspiration absorbing pad and which can be removed for laundering. U.S. Pat. No. 757,854 and U.S. Pat. No. 3,019,028 each illustrate removable visors attached to head bands. U.S. Pat. No. 3,769,380 teaches a visor and sweat band made of a special absorbing material, but in which the visor is not removable from the sweat band, while U.S. Pat. No. 1,232,992 has a cap with a removable visor. U.S. Pat. No. 1,484,042 and U.S. Pat. No. 535,143 also illustrate visors. In contrast to these prior patents, the present invention provides an ordinary elasticized sweat band for use in sports in which a rapidly and easily attachable sun-shading visor is quickly attached as desired by the user, and may be detached when not needed and for laundering the sweat band. In addition, the visor of the present invention is of an injection molded plastic which is both attractive and designed for more complete shading of the user's eyes. A cap is also provided with an elasticized sweat band which can be removed for laundering or quickly replaced.

SUMMARY OF THE INVENTION

The present invention provides a sweat band of a moisture absorbing material such as terrycloth which may be elasticized for holding around the head of an individual user and which has a strip of hook and loop material, such as velcro, attached thereto. A molded plastic or polymer sun visor having a curved portion shaped to fit adjacent the forehead of the user has a strip of hook and loop fastening material attached to the curved portion of the visor so that the fastening material on the sun visor can be quickly attached to the material located on the sweat band. Thus, the user of the sweat band can rapidly put the sweat band on and remove it as well as launder the sweat band. A cap is provided having a portion of the crown and sweat band removed and a portion of hook and loop material attached to the sweat band for removably attaching a second moisture absorbing sweat band which can expand through the opening in the crown.

BRIEF DESCRIPTION OF THE DRAWINGS

Other objects, features, and advantages of the present invention will be apparent from the written description and the drawings, in which:

FIG. 1 is a perspective view of the combined sweat band and visor;

FIG. 2 is an exploded perspective view of the sweat band and visor;

FIG. 3 is a perspective view of an alternate embodiment of the sweat band;

DESCRIPTION OF THE PREFERRED EMBODIMENTS

Figure 4:
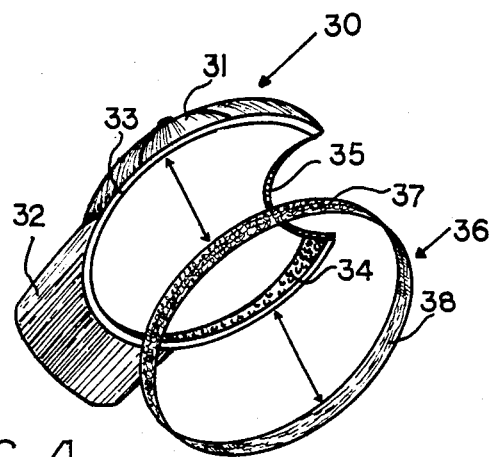
FIG. 4 is an exploded perspective view of a cap embodiment.
Figure 6:
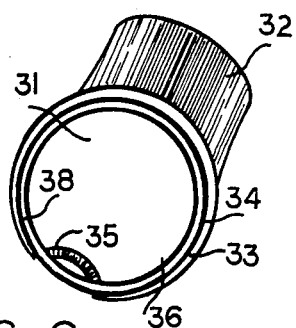
FIG. 6 is a bottom elevation of the cap of FIGS. 4 and 5.

Referring now to FIGS. 1 and 2 of the drawings, a sweat band and visor combination 10 has a sweat band 11 made of a terrycloth material with elasticized material therein for stretching the sweat band to fit the head of the user. The sweat band has an elongated strip of hook and loop material 12 such as VELCRO, attached to the exterior of the circular band 11 which material may be one half of a hook and loop combination in which a large plurality of small loops are woven into a base on one portion while the other coacting portion 13 may have a generally random hooking polymer material which when placed against the loops will engage and adhere thereto in a fairly rigid manner. The material 13 is attached to a concave curved portion 14 of a sun visor 15 having a visor portion 16 for shading the eyes of the user. The curve portion 14 is shaped to fit the forehead of the individual user so that the concave curved portion having the hooking material 13 attached thereto can engage the loop material 12 of the sweat band 11. The curve portion 14, advantageously, has protrusions 17 protruding a portion of the way around the forehead to provide additional strength and reinforcement for the attachment of the hooking material 13 to the loop material 12 for additional support of the visor on the head so as to provide rigid support to a rapidly moving individual participating in a sport.

FIG. 3 illustrates an alternate sweat band 18 made of terrycloth or other similar sweat absorbing material 20 and having an elongated strip of loop material 21 attached thereto for receiving the visor 15 hooking material 12. This sweat band is different inasmuch as it has a pair of straps 22 and 23 connected with buckles 24 for adjusting the sweat band to the head of the user which in turn gives greater support than an elasticized band 11 might have for a particular user, especially where great variations in the size of the user's head exist.

It should be clear that the present invention not only allows for the very rapid attachment of the visor 15 to the sweat band 11 if the sun is forward of the user in a sporting activity and for the quick removal of the visor if not desired by the user, but adds greater strength by the long curved portion 14 allowing greater connecting area between the strips of hook and loop material 12 and 13 as well as support around the front and sides of the forehead. Advantageously, this allows a sun visor 15 to be made of a polymer material so that it can be injection molded into a colorful and functionally well-shaped sun visor for mass production.

Figure 5:
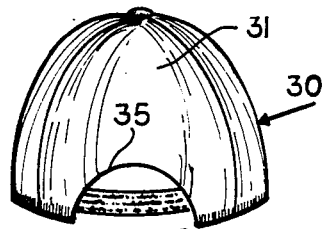
FIG. 5 is a rear elevation of the cap of FIG. 4.
Figure 7:
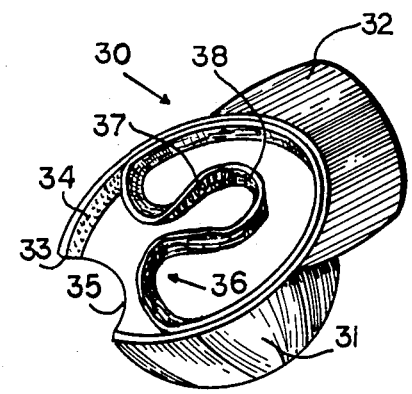
FIG. 7 is a bottom perspective view of the cap having the sweat band partially removed.

Turning now to the embodiment illustrated in FIGS. 4, 5, 6 and 7, a cap 30 is illustrated having a crown portion 31, a visor portion 32 and a sweat band 33. The sweat band 33 has had a strap of hook and loop material 34 fixedly attached thereto, such as by sewing, or the like, while the crown portion 31 has had a portion 35 removed therefrom on the rear of the cap 30, along with the rear portion of the cap's sweat band 33, which has also been removed. An elasticized terrycloth sweat band 36 has a portion of the exterior circumference lined with a second portion of hook and loop material 37 opposite from that of 34, so that the material 37 can be removably attached to the material 34. A portion 38 of the sweat band 36 does not have the hook and loop material attached, and this portion extends across the opening 35 in the crown 31 and sweat band 33 when it is attached to the hat, as illustrated in FIG. 5. The opening 35 allows the sweat band 36 to expand, and thereby snugly fit the user of a variety of sizes of hats, and simultaneously provides a place to get the hand in to grasp the portion 38 of the sweat band 36 to remove the sweat band 36 from the hat 30. Thus, the sweat band may be readily laundered and replaced in the hat, or may be replaced with a new sweat band when worn out, thereby substantially increasing the life of the cap and more readily absorbing the sweat on the forehead and head of the user. It should be clear at this point that while a cap 30 having a flexible crown 31 has been illustrated, that a hard hat could also be used, such as used by baseball players for the protection of the head, without departing from the spirit and scope of the invention. It should, accordingly, be clear that the present invention is not to be construed as limited to the particular forms shown, which are to be considered illustrative rather than restrictive.

We claim:

1. A sweat band visor apparatus comprising in combination:
   a sweat band made out of moisture absorbing material and shaped to fit around the forehead of a user;
   at least one strip of hook and loop material attached to said sweat band and extending a portion of a way around said sweat band; and
   a moldable plastic sun visor having an elongated, arcuate surface curved for fitting adjacent a person's forehead and extending to the sides of the forehead of a user, said arcuate surface having a strip of hook and loop material attached thereto for attaching to the coacting hook and loop material on said sweat band, thereby allowing rapid attachment or removal of a sun visor as needed by the user.

2. The apparatus in accordance with claim 1, in which said sweat band is terrycloth having an elasticized material therein.

3. The apparatus in accordance with claim 3, in which said sweat band has an adjustable strap for adjusting the sweat band to different sized heads.

4. An adjustable eye-shade comprising:
   (a) a head band positionable in retained relationship on a person's head,
   (b) a visor element of flexible material forming an eye-shading panel, said panel having a peripheral edge which includes an inwardly curved portion that is adapted to cooperatively interfit with said headband, and
   (c) connecting means for selectively interconnecting said peripheral edge of said visor element to said headband, said connecting means being a two element structure wherein one of said elements includes a loop surface and the other a hook surface which are cooperatively interengageable for subsequent disengagement, one element of said connecting means fastened to said headband at an exteriorally facing surface thereof and the other element secured to the inwardly curved peripheral edge portion of said visor element.

5. An adjustable eye-shade according to claim 1 wherein said headband has a vertical dimension substantially greater than the thickness of said visor element.

6. An adjustable eye-shade according to claim 1 wherein the loop surface element of said connecting means is attached to said visor element and the hook surface element is attached to said headband.

7. An adjustable eye-shade according to claim 1 wherein said visor element is formed from a resin material.

8. A sweat band visor comprising:
   (a) a sweat band, at least a portion of which is an elastic, moisture-absorbing fabric and stretchable to fit around the head of a user;
   (b) at least one strip of hook and loop material attached to, and extending around only a portion of the outer periphery of said sweat band; and
   (c) a moldable plastic sun visor having an elongated arcuate surface curved for fitting adjacent a person's forehead and extending to the side of the forehead of the user, said arcuate surface having a strip of hook and loop material attached thereto about the inside periphery of said arcuate surface for attaching to the co-acting hook and loop material of said sweat band, thereby allowing rapid attachment or removal of a sun visor to said sweat band.

9. A sweat band and visor apparatus as recited in claim 8, wherein the loop surface element of said hook and loop material is attached to said plastic sun visor and the hook portion of said hook and loop material is attached to said sweat band.

10. The sweat band and sun visor apparatus recited in claim 8 wherein said head band has a vertical dimension substantially greater than the thickness of said visor element.

11. The sweat band and sun visor apparatus recited in claim 8 wherein the hook and loop material of said sun visor is attached to the inside of said arcuate surface.

* * * * *